United States Patent [19]
Takeuchi et al.

[11] Patent Number: 5,321,182
[45] Date of Patent: Jun. 14, 1994

[54] PROCESS FOR PREPARING 2-ALKYL-6-ETHYLNAPHTHALENE

[75] Inventors: Genki Takeuchi; Mituru Shiroshita; Kazuyoshi Kariu; Yasuhiro Shimoura, all of Kitakyushu, Japan

[73] Assignee: Nippon Steel Chemical Co., Ltd., Tokyo, Japan

[21] Appl. No.: 858,686

[22] Filed: Mar. 27, 1992

[30] Foreign Application Priority Data

Jul. 27, 1990 [JP] Japan .................................. 2-199997
Sep. 4, 1990 [JP] Japan .................................. 2-234279

[51] Int. Cl.$^5$ .......................... C07C 2/66; C07C 5/52
[52] U.S. Cl. ...................................... 585/475; 585/471
[58] Field of Search ............................. 585/471, 475

[56] References Cited

U.S. PATENT DOCUMENTS

| | | | |
|---|---|---|---|
| 3,233,002 | 2/1966 | Kovach et al. | 585/471 |
| 3,855,328 | 12/1974 | Hedge | 585/471 |
| 3,870,745 | 3/1975 | Angstadt | 585/471 |
| 4,112,008 | 9/1978 | Marcilly | 585/471 |
| 4,873,386 | 10/1989 | Hagen et al. | 585/471 |
| 5,001,295 | 3/1991 | Angevine et al. | 585/467 |
| 5,171,917 | 12/1992 | Hagen et al. | 585/474 |

FOREIGN PATENT DOCUMENTS

| | | |
|---|---|---|
| 58-204817 | 11/1983 | Japan . |
| 63-14737 | 1/1988 | Japan . |
| 64-68329 | 3/1989 | Japan . |
| 1-299237 | 12/1989 | Japan . |
| 2-295936 | 12/1990 | Japan . |
| 2-300141 | 12/1990 | Japan . |

OTHER PUBLICATIONS

Shimada et al, Bulletin of the Chemical Society of Japan, vol. 48(11), pp. 3306–3308 (1975).

*Primary Examiner*—Anthony Mc Farlane
*Attorney, Agent, or Firm*—Birch, Stewart, Kilasch & Birch

[57] ABSTRACT

2-Alkyl-6-ethylnaphthalene is prepared selectively and efficiently by the reaction of at least one kind of feed naphthalene selected from naphthalene and 2-alkylnaphthalenes with polyethylbenzenes at 50° to 400° C. in the presence of a solid acid catalyst.

11 Claims, No Drawings

PROCESS FOR PREPARING 2-ALKYL-6-ETHYLNAPHTHALENE

CROSS-REFERENCE TO RELATED APPLICATION

This application is a Continuation-in-Part of PCT International Application No. PCT/JP91/01004 which was filed on Jul. 25, 1991. The entire contents of this PCT international application are hereby incorporated by reference.

FIELD OF TECHNOLOGY

This invention relates to a process for preparing 2-alkyl-6-ethylnaphthalene which is useful as raw material for 2,6-naphthalenedicarboxylic acid.

RELATED TECHNOLOGIES 2,6-Naphthalenedicarboxylic acid is useful as raw material for polymers such as polyesters and as intermediate for dyes. One of the commercially advantageous processes for the production of 2,6-naphthalenedicarboxylic acid is the liquid-phase oxidation of 2,6-diisopropylnaphthalene. This process, however, is not necessarily satisfactory because of some difficulty in the oxidation of the isopropyl group to the carboxyl group. By comparison therewith, the liquid-phase oxidation of ethyl group-containing naphthalene, typically 2,6-diethylnaphthalene, proceeds in high yield and is expected to provide a low-cost process for the preparation of 2,6-naphthalenedicarboxylic acid.

There is consequently a strong desire for efficient production of 2-alkyl-6-ethylnaphthalene. However, the commonly known reaction of naphthalene or its derivatives such as methylnaphthalene with an ethylating agent such as ethylene and ethyl halide in the presence of an acid catalyst such as $AlCl_3$ progresses with low selectivity to 2-alkyl-6-ethylnaphthalene accompanied by extensive formation of pitch from polymerization of naphthalene and its derivatives. Thus a process based on this reaction is not suited for commercial practice.

Processes for the preparation of ethylnaphthalenes by the reaction of naphthalene with ethylbenzenes are described, for example, in U.S. Pat. No. 4,873,386 and Bull. Chem. Soc. Jpn., 48, 3306–3308 (1975). The use of $AlCl_3$ or $FeCl_3$, a Lewis acid soluble in the reaction system, as catalyst in these processes has presented the following problems: the steps for water washing and neutralization must be provided for removal of the catalyst after completion of the reaction; acidic waste water containing $AlCl_3$ is discharged in large quantities; the reaction is difficult to run on a continuous basis; and acid-resistant materials are required for the reactors. In addition, a Lewis acid catalyst such as $AlCl_3$ causes extensive formation of pitch by polymerization of naphthalene and its derivatives.

The transisopropylation of 2-methylnaphthalene in the presence of a catalyst consisting of sulfuric acid supported on zirconia is described in Japan Kokai Tokkyo Koho No. 1-299,237 (1989). The process, however, yields 2,6-dialkylnaphthalene and 2,7-dialkylnaphthalene at a ratio of 1.12 and cannot be regarded as a selective process for the preparation of 2,6-dialkylnaphthalene.

The transethylation of aromatic compounds in the presence of a solid acid catalyst is described in Japan Kokai Tokkyo Koho No. 64-68,329 (1989) but no mention is made on the selective ethylation of naphthalene.

The methylation of 2-alkylnaphthalene in the presence of a zeolite catalyst is described in U.S. Pat. No. 5,001,295. The conversion observed in the process is too low to justify commercialization. As indicated here, there is a tendency in general for the methylation to achieve a higher conversion with difficulty.

DISCLOSURE OF THE INVENTION

It is an object of this invention to provide a process for preparing 2-alkyl-6-ethylnaphthalene selectively and efficiently by ethylation in the presence of a solid acid catalyst.

The present inventors have conducted extensive studies to establish the aforesaid process, found that the use of a solid acid catalyst and polyethylbenzenes as alkylating agent permits efficient and selective preparation of 2-alkyl-6-ethylnaphthalene, and completed this invention.

This invention accordingly relates to a process for preparing 2-alkyl-6-ethylnaphthalene which comprises allowing naphthalene and/or alkylnaphthalene to react with polyethylbenzenes at 50° to 400° C. in the presence of a solid acid catalyst.

The solid acid catalysts to be used in this invention belong to a group of catalysts commonly known as such, for example, silica-alumina, zeolites, composite metal oxides, solid phosphoric acid, heteropoly acids, and ion exchange resins. They should preferably have pores with a diameter of 7.2 Å or more and contain 0.1 mol/kg or more of acid sites with a differential heat of adsorption of ammonia of 85 kjoul/mol or more. More preferably, they should contain 0.1 mol/kg or more of acid sites with a differential heat of adsorption of ammonia of 85 kjoul/mol or more and 0.01 mol/kg or more of acid sites with a differential heat of adsorption of ammonia of 130 kjoul/mol or more. The differential heat of adsorption of ammonia is defined in Bull. Chem. Soc. Jpn., 48, 3576 (1975). Solid acid catalysts with a pore diameter of 7.2 Å or less do not provide enough space for the transethylation to take place between the naphthalene and benzene rings, thus yielding low conversion. On the other hand, it is not possible to raise the yield of 2-alkyl-6-ethylnaphthalene while maintaining the selectivity at a high level if solid acid catalysts contain less than 0.1 mol/kg of acid sites with a differential heat of adsorption of ammonia of 85 kjoul/mol or more.

The solid acid catalysts which meet the aforesaid requirements and are readily available commercially include silica-alumina, zeolites, and ion exchange resins. Desirable among zeolites are faujasite type, particularly Y type and X type, or those chemically treated by such means as ion exchange, dealumination, fluorination, and steaming. Zeolites with a pore diameter of less than 7.2 Å, for example, L type zeolites, mordenite type, and ZSM 5, yield low conversion, probably because the reaction takes place only on their surface. Silica-alumina often shows less surface acidity than zeolites, but it is more favorable as catalyst of this invention because it is amorphous and does not hinder the reaction unlike small-pore L type or mordenite type zeolites. Silica-alumina can also be chemically treated by ion exchange, dealumination, fluorination, or steaming before submission to the reaction. As for ion exchange resins, those with good heat resistance are desirable as they allow a wider latitude in selection of reaction conditions. An example of such ion exchange resins is Nafion (tradename of DuPont), a perfluorosulfonic acid type cation exchange resin. It is desirable for the solid acid catalysts to contain 0.1 mol/kg or more of acid sites with a differential heat of adsorption of ammonia of 85 kjoul/mol or more. In the presence of more than 3 mol/kg of acid sites, the rate of separation of carbonaceous matter increases with a resultant decrease in catalyst life. Of the deactivated solid acid catalysts, metal oxides such as zeolites can readily be regenerated by calcining them with nitrogen-diluted air at approximately 500° C. to remove the carbonaceous matter.

Naphthalene or alkylnaphthalene is used as raw material in this invention. Alkylnaphthalene occurs as 1-alkylnaphthalene or 2-alkylnaphthalene and 2-alkylnaphthalene, or a mixture containing a large proportion thereof is advantageous. Naphthalene or alkylnaphthalene is used alone, or as a mixture. The use of 2-alkylnaphthalene, or a mixture containing a large proportion thereof raises the selectivity and yield of 2-alkyl-6-ethylnaphthalene. Methylnaphthalene or ethylnaphthalene is desirable as alkylnaphthalene. Naphthalene with an alkyl group having 3 or more carbon atoms is oxidized in the liquid phase to 2,6-naphthalenedicarboxylic acid with difficulty. It is desirable to keep the basic nitrogen content in the feed naphthalene or alkylnaphthalene at 50 ppm or less, preferably 20 ppm or less.

Comparison of 2-methylnaphthalene with 2-ethylnaphthalene as raw material seems to favor 2-ethylnaphthalene because it not only shows higher selectivity to 2-alkyl-6-ethylnaphthalene, but also facilitates the separation or recycle of the by-products and the unreacted starting material because of the absence of a mixture of the methyl and ethyl groups in the reaction system. On the other hand, naphthalene is favorable for its ready availability. It is therefore desirable to use a feed containing a major portion of naphthalene and/or 2-ethylnaphthalene, preferably 70% by weight or more.

The polyethylbenzenes to be used as ethylating agent comprise one or a mixture of two or more compounds selected from 1,2-diethylbenzene, 1,3-diethylbenzene, 1,4-diethylbenzene, 1,2,3-triethylbenzene, 1,2,4-triethylbenzene, 1,3,5-triethylbenzene, 1,2,3,4-tetraethylbenzene, 1,2,3,5-tetraethylbenzene, 1,2,4,5-tetraethylbenzene, pentaethylbenzene, and hexaethylbenzene, with the molar ratio of ethyl group to benzene ring controlled preferably at 2 or more, more preferably at 3.0 or more, and most preferably at 3.5 or more. A lower molar ratio retards the reaction. Most desirable are triethylbenzenes, tetraethylbenzenes, or a mixture containing a major proportion of one or both of them. Polyethylbenzenes containing diethylbenzenes or triethylbenzenes as major components can be obtained from a high-boiling fraction available as by-product in the preparation of ethylbenzene and they can be ethylated further with ethanol or ethylene to yield polyethylbenzenes, mainly containing tetraethyl-benzenes.

The reaction temperature is 50° to 400° C., preferably 50° to 300° C., more preferably 50° to 280° C., and most preferably from 50° C. to less than 200° C. In the cases where the reaction temperature is equal to or below the melting point of the reactants, it is possible to use an inert solvent such as Decalin and n-paraffin. Below 50° C., the reaction rate is too low to be commercially viable. Above 400° C., the selectivity to 2-alkyl-6-ethylnaphthalene drops, accompanied by deethylation, decomposition of the ethyl group, polymerization of the ethyl group, and discoloration of the products. Normally, the lower the reaction temperature, the higher the selectivity to 2-alkyl-6-ethylnapthhalene becomes. Where a high reaction temperature is chosen, it is possible to obtain high selectivity to 2-alkyl-6-ethylnaphthalene by reducing the reaction time.

The reaction pressure ranges from ambient pressure to 100 kg/cm$^2$, preferably from ambient pressure to 50 kg/cm$^2$. In consideration of the catalyst life, it is adequate to set the pressure at such a level as to cause the reactants and the products to remain liquid in the reactor. A pressure set higher than necessary does not adversely affect the reaction, but the pressure does not used to be particularly high.

The reaction may be carried out either in continuous flow or in batch. A fixed-bed continuous flow process is suitable for commercial large-volume production and a batch process for small-volume production.

When the reaction is carried out under the above-mentioned conditions, the transethylation occurs wherein naphthalene and/or alkylnaphthalene is ethylated, and ethylbenzenes are deethylated. The mixture after completion of the reaction contains naphthalene, alkylnaphthalenes, dialkylnaphthalenes, trialkylnaphthalenes, benzene, ethylbenzene, and diethylbenzenes.

The reaction time or contact time is 10 minutes to 20 hours, preferably 20 minutes to 10 hours, although it may vary with other conditions. It is possible to control the conversion of feed naphthalenes and to raise the proportion of 2-alkyl-6-ethylnaphthalene in the product dialkylnaphthalenes by properly selecting the reaction time, reaction temperature, and other conditions. It is desirable to attain a 2,6-isomer to 2,7-isomer ratio of 1.0 or more, preferably 1.5 or more, more preferably 2.0 or more, in dialkylnaphthalenes.

As mentioned above, the mixture after completion of the reaction contains ethylbenzenes, naphthalene, alkylnaphthalenes, dialkylnaphthalenes, trialkylnaphthalenes, and tetraalkylnaphthalenes in addition to 2-alkyl-6-ethylnaphthalene. The mixture is first distilled to recover a fraction containing 2-alkyl-6-ethylnaphthalene and a separatory procedure such as cooling crystallization, pressure crystallization, adsorption, and adduct formation is applied to said fraction to separate 2-alkyl-6-ethylnaphthalene. Where the purity of the separated material is not sufficiently high, it can be raised even to 100% by recrystallization from a solvent such as methanol, ethanol, and isopropanol.

The residue containing naphthalene, alkylnaphthalene, dialkylnaphthalenes, trialkylnaphthalenes, tetraalkylnaphthalenes, and others after the separation of 2-alkyl-6-ethylnaphthalene is recycled to the reactor as raw material for the preparation of 2-alkyl-6-ethylnaphthalene.

DETAILED DESCRIPTION OF THE PREFERRED EMBODIMENTS

This invention will be described in detail below with reference to the accompanying examples, but not limited thereto.

EXAMPLES 1–21

Naphthalene or its alkyl derivative and polyethylbenzenes as reactants and a solid acid catalyst were introduced into an autoclave equipped with a stirrer and allowed to react under the conditions shown in Table 1.

The solid acid catalysts used are Y type zeolite ① (Y-①), Y type zeolite ② (Y-②), perfluorosulfonic acid type ion exchange resin (Nafion from DuPont) (IER), and silica-alumina (S-A).

The Y type zeolites have pores with a diameter of 7.4 Å and the molar ratio (SiO$_2$/Al$_2$O$_3$) is 6 for Y type zeolite ①, and 100 for Y type zeolite ②, the latter having been prepared by treating the former with HCl in order to raise the ratio SiO$_2$/Al$_2$O$_3$. Y type zeolite ① contains 1.3 mol/kg of acid sites with a differential heat of adsorption of ammonia of 85 kjoul/mol or more, Y type zeolite ② 0.4 mol/kg, the silica-alumina 0.2 mol/kg, and the perfluorosulfonic acid type ion exchange resin approximately 1 mol/kg. Moreover, Y type zeolite ① has 0.5 mol/kg of acid sites with a differential heat of adsorption of ammonia of 130 kjoul/mol or more and Y type zeolite ② 0.02 mol/kg. The silica-alumina mainly has pores with a diameter of 20 to 100 Å while the perfluorosulfonic acid type ion exchange resin mainly has pores with a diameter of 10 Å or more.

A 55:45 mixture of 1,2,3,4-tetraethylbenzene and 1,2,3,5-tetraethylbenzene was used as ethylating agent.

Naphthalene (N), 2-methylnaphthalene (2-MN), or 2-ethylnaphthalene (2-EN) was used as feed naphthalene.

The proportion by weight of dialkylnaphthalenes in the compounds containing a naphthalene ring in the reaction products is shown in Table 3 together with the selectivity and yield of 2-alkyl-6-ethylnaphthalene.

EXAMPLES 22–25

Into an autoclave equipped with a stirrer were introduced naphthalene or 2-ethylnaphthalene as feed, L type zeolite or mordenite as catalyst, and a mixture of 1,2,3,4-tetraethylbenzene and 1,2,3,5-tetraethylbenzene as ethylating agent and the reaction was carried out under the conditions shown in Table 2.

The L type zeolite has 1.4 mol/kg of acid sites with a differential heat of adsorption of ammonia of 85 kjoul/mol or more and the mordenite 1.6 mol/kg. The results are shown in Table 4.

COMPARATIVE EXAMPLES 1–5

Naphthalene and the silica-alumina catalyst were introduced into an autoclave equipped with a stirrer and the reaction was carried out with continuous introduction of ethylene as ethylating agent into the autoclave under the conditions shown in Table 2. The results are shown in Table 4.

EXAMPLE 26

A fixed-bed flow reactor was filled with 20 cc of Y type zeolite ① as catalyst, the same as used in Example 12, and naphthalene and a mixture of triethylbenzene isomers were fed continuously at WHSV (weight hourly space velocity)=1 hr$^{-1}$. The reaction temperature was 120° C. and the molar ratio of naphthalene to triethylbenzenes was unity. Table 4 shows the proportion by weight of dialkylnaphthalenes in the compounds containing naphthalene ring in the reaction products sampled during the 8th hour after the start of the reaction and also the selectivity and yield of 2,6-diethylnaphthalene.

EXAMPLE 27

A fixed-bed flow reactor was filled with 20 cc of Y type zeolite ② as catalyst, the same as used in Example 1, and 2-ethylnaphthalene and a mixture of tetraethylbenzene isomers were fed continuously at WHSV=1 hr$^{-1}$. The reaction temperature was 140° C. and the molar ratio of 2-ethylnaphthalene to tetraethylbenzenes was 3. Table 4 shows the proportion by weight of dialkylnaphthalenes in the compounds containing naphthalene ring in the reaction products sampled during the 25th hour after the start of the reaction and also the selectivity and yield of 2,6-diethylnaphthalene.

Table 5 also shows the proportion by weight of dialkylnaphthalenes in the compounds containing naphthalene ring in the reaction products sampled during the 720th hour, the 1440th hour and the 1860th hour after the start of the reaction and also the selectivity and yield of 2,6-diethylnaphthalene together with the result of the reaction products sampled during the 25th hour.

EXAMPLE 28

The reaction was carried out as in Example 27 except replacing the catalyst with Y type zeolite ①. Table 4 shows the proportion by weight of dialkylnaphthalenes in the compounds containing naphthalene ring in the reaction products sampled during the 50th hour after the start of the reaction and also the selectivity and yield of 2,6-diethylnaphthalene.

TABLE 1

| Example No. | Reaction temp. (°C.) | Reaction time, (min.) | N | 2-MN | 2-EN | TEB | Y-① | Y-② | IER | S-A |
|---|---|---|---|---|---|---|---|---|---|---|
| 1 | 110 | 240 | 31 | — | — | 119 | — | 45 | — | — |
| 2 | 110 | 480 | 31 | — | — | 119 | — | 45 | — | — |
| 3 | 110 | 1,020 | 31 | — | — | 119 | — | 45 | — | — |
| 4 | 110 | 60 | — | — | 31 | 119 | — | 45 | — | — |
| 5 | 110 | 240 | — | — | 31 | 119 | — | 45 | — | — |
| 6 | 110 | 360 | — | — | 31 | 119 | — | 45 | — | — |
| 7 | 130 | 60 | — | — | 31 | 119 | — | 45 | — | — |
| 8 | 130 | 120 | — | — | 31 | 119 | — | 45 | — | — |
| 9 | 140 | 60 | — | — | 31 | 119 | — | 45 | — | — |
| 10 | 120 | 360 | — | 31 | — | 119 | — | 45 | — | — |
| 11 | 150 | 240 | — | 31 | — | 119 | — | 45 | — | — |
| 12 | 70 | 180 | — | — | 31 | 119 | 45 | — | — | — |
| 13 | 80 | 120 | — | — | 31 | 119 | 45 | — | — | — |
| 14 | 100 | 90 | — | — | 15 | 119 | 45 | — | — | — |
| 15 | 180 | 420 | — | — | 31 | 119 | — | — | 45 | — |
| 16 | 200 | 60 | — | — | 31 | 119 | — | — | 60 | — |
| 17 | 175 | 480 | 60 | — | 90 | — | — | — | — | 45 |
| 18 | 200 | 150 | 60 | — | 90 | — | — | — | — | 45 |
| 19 | 200 | 270 | 60 | — | 90 | — | — | — | — | 45 |
| 20 | 250 | 90 | 60 | — | 90 | — | — | — | — | 45 |

TABLE 1-continued

| Example No. | Reaction temp. (°C.) | Reaction time, (min.) | Amount charged (parts by weight) | | | | | | |
|---|---|---|---|---|---|---|---|---|---|
| | | | N | 2-MN | 2-EN | TEB | Y-① | Y-② | IER | S-A |
| 21 | 175 | 300 | — | — | 31 | 119 | — | — | — | 45 |

(Note) N = Naphthalene; 2-MN = 2-Methylnaphthalene; 2-EN = 2-Ethylnaphthalene; TEB = Tetraethylbenzenes; Y-① = Y type zeolite ①; Y-② = Y type zeolite ②; IER = Perfluorosulfonic acid type ion exchange resin; S-A = Silica-alumina

TABLE 2

| Example No. | Reaction temp. (°C.) | Reaction time (min.) | Amount charged (parts by weight) | | | | | | |
|---|---|---|---|---|---|---|---|---|---|
| | | | N | 2-EN | TEB | E | S-A | L | Mor |
| Example | | | | | | | | | |
| 22 | 110 | 360 | — | 31 | 119 | — | — | 45 | — |
| 23 | 130 | 240 | — | 31 | 119 | — | — | 45 | — |
| 24 | 110 | 360 | — | 31 | 119 | — | — | — | 45 |
| 25 | 130 | 240 | — | 31 | 119 | — | — | — | 45 |
| Comparative Example | | | | | | | | | |
| 1 | 250 | 30 | 103 | — | — | 11 | 45 | — | — |
| 2 | 250 | 70 | 103 | — | — | 23 | 45 | — | — |
| 3 | 250 | 160 | 103 | — | — | 35 | 45 | — | — |
| 4 | 300 | 30 | 103 | — | — | 12 | 45 | — | — |
| 5 | 300 | 60 | 103 | — | — | 23 | 45 | — | — |

(Note) N = Naphthalene; 2-EN = 2-Ethylnaphthalene; TEB = Tetraethylbenzenes; E = Ethylene; S-A = Silica-alumina; L = L type zeolite; Mor = Mordenite

TABLE 3

| Example No. | Conversion of naphthalenes (%) | Yield of dialkyl-naphthalenes (wt. %) | Proportion of dialkylnaphthalene isomers (%) | | | | |
|---|---|---|---|---|---|---|---|
| | | | 2,6- | 2,7- | 1,6- | 1,7- | Others |
| 1 | 45.2 | 17.4 | 54.6 | 22.0 | 12.2 | 7.5 | 3.7 |
| 2 | 77.2 | 44.0 | 50.3 | 25.2 | 12.7 | 7.6 | 4.3 |
| 3 | 95.2 | 62.6 | 49.1 | 27.8 | 11.8 | 6.2 | 5.1 |
| 4 | 11.7 | 12.3 | 72.6 | 19.1 | 5.2 | 2.6 | 0.5 |
| 5 | 63.0 | 62.3 | 65.9 | 22.4 | 7.8 | 3.1 | 0.8 |
| 6 | 78.0 | 73.4 | 63.9 | 23.3 | 8.5 | 3.2 | 1.1 |
| 7 | 45.8 | 48.3 | 66.6 | 20.3 | 7.8 | 4.3 | 1.0 |
| 8 | 74.1 | 69.7 | 65.8 | 20.8 | 8.7 | 3.5 | 1.2 |
| 9 | 81.2 | 72.9 | 63.4 | 22.5 | 9.4 | 3.4 | 1.3 |
| 10 | 28.3 | 29.4 | 61.5 | 24.5 | 6.4 | 5.1 | 2.5 |
| 11 | 80.1 | 67.4 | 53.4 | 23.6 | 10.2 | 4.5 | 8.3 |
| 12 | 64.6 | 58.1 | 53.1 | 24.4 | 12.1 | 6.0 | 4.4 |
| 13 | 82.7 | 62.3 | 50.1 | 24.8 | 15.0 | 5.3 | 4.8 |
| 14 | 73.2 | 61.0 | 51.0 | 24.6 | 14.9 | 5.3 | 4.2 |
| 15 | 43.8 | 35.0 | 53.0 | 24.0 | 14.6 | 3.6 | 4.8 |
| 16 | 74.2 | 60.3 | 50.5 | 26.3 | 14.5 | 4.2 | 4.5 |
| 17 | 39.0 | 11.5 | 43.4 | 24.3 | 12.2 | 8.4 | 11.6 |
| 18 | 31.5 | 7.6 | 43.1 | 24.8 | 13.0 | 9.2 | 10.0 |
| 19 | 47.7 | 15.2 | 40.0 | 26.0 | 13.2 | 9.3 | 11.6 |
| 20 | 51.2 | 7.6 | 35.3 | 26.5 | 15.1 | 10.7 | 12.5 |
| 21 | 46.4 | 43.4 | 48.4 | 27.3 | 14.1 | 5.1 | 5.1 |

(Notes) The conversion of naphthalenes indicates the conversion of feed naphthalene, 2-methylnaphthalene, or 2-ethylnaphthalene. The yield of dialkylnaphthalenes indicates the proportion by weight of dialkylnaphthalenes in the compounds containing naphthalene ring. The designation "2,6-" refers to 2,6-dialkylnaphthalene. The designation "others" refers to the sum of other dialkylnaphthalenes.

TABLE 4

| Example | Conversion of naphthalenes (%) | Yield of dialkyl-naphthalenes (wt. %) | Proportion of dialkylnaphthalene isomers (%) | | | | |
|---|---|---|---|---|---|---|---|
| | | | 2,6- | 2,7- | 1,6- | 1,7- | Others |
| Example | | | | | | | |
| 22 | 1.7 | 1.2 | 44.6 | 28.6 | 12.0 | 7.2 | 7.6 |
| 23 | 3.6 | 2.2 | 41.9 | 30.6 | 11.1 | 8.0 | 8.4 |
| 24 | 0.6 | 0.3 | 61 | 39 | 0 | 0 | 0 |
| 25 | 1.2 | 0.5 | 55 | 29 | 10 | 6 | 0 |
| 26 | 92.7 | 56.0 | 45.3 | 28.4 | 13.6 | 7.0 | 5.7 |
| 27 | 78.4 | 67.4 | 61.6 | 22.0 | 11.4 | 3.0 | 2.0 |
| 28 | 95.1 | 62.5 | 55.4 | 22.9 | 13.7 | 3.7 | 4.3 |
| Comparative Example | | | | | | | |
| 1 | 23.7 | 4.4 | 16.0 | 15.0 | 10.2 | 9.8 | 49.0 |
| 2 | 57.8 | 18.1 | 15.6 | 14.3 | 11.0 | 11.0 | 48.0 |
| 3 | 76.3 | 26.3 | 17.3 | 15.3 | 10.8 | 10.9 | 44.3 |
| 4 | 27.1 | 4.5 | 15.5 | 15.2 | 10.5 | 10.6 | 48.3 |
| 5 | 50.3 | 14.0 | 17.3 | 16.2 | 10.0 | 9.6 | 46.9 |

(Notes) The conversion of naphthalenes indicates the conversion of feed naphthalene, 2-methylnaphthalene, or 2-ethylnaphthalene. The yield of dialkylnaphthalenes indicates the proportion by weight of dialkylnaphthalenes in the naphthalene ring-containing compounds. The designation "2,6-" refers to 2,6-dialkylnaphthalene. The designation "others" refers to the sum of other dialkylnaphthalenes.

TABLE 5

(Example 27)

| Time (hrs.) | Temp. (°C.) | Conversion of naphthalenes (%) | Yield of dialkyl-naphthalenes (wt. %) | Proportion of dialkylnaphthalene isomers (%) | | | | |
|---|---|---|---|---|---|---|---|---|
| | | | | 2,6- | 2,7- | 1,6- | 1,7- | Others |
| 720 | 202 | 73.2 | 63.3 | 53.3 | 21.0 | 14.6 | 5.8 | 5.3 |
| 1440 | 222 | 77.8 | 63.8 | 49.6 | 21.7 | 16.0 | 6.8 | 5.9 |
| 1860 | 222 | 65.9 | 58.0 | 49.9 | 21.5 | 15.0 | 7.1 | 6.1 |

INDUSTRIAL APPLICABILITY

As described above, the process of this invention can produce 2-alkyl-6-ethylnaphthalene selectively and efficiently and the oxidation of 2-alkyl-6-ethylnaphthalene can yield 2,6-naphthalenedicarboxylic acid which is useful as raw material for polyesters.

What is claimed is:

1. A process for preparing 2,6-diethylnaphthalene, which comprises reacting at least one kind of feed naphthalene selected from naphthalene and 2-ethylnaphthalene with polyethylbenzenes, having a molar ratio of ethyl group to benzene ring of 2 or more, at 50° to 200° C. in the presence of a solid acid catalyst having pores with a diameter of 7.2 Å or more and containing 0.1 mol/kg or more of acid sites with a differential heat of absorption of ammonia of 85 kjoul/mol or more, and wherein a ratio of 2,6-diethylnaphthalene to 2,7-diethylnaphthalene in the product is 1.5 or more.

2. The process according to claim 1 wherein said molar ratio of ethyl group to benzene ring in said polyethylbenzenes is 3 or more.

3. The process according to claim 1 wherein said solid acid catalyst has the structure of a Y zeolite.

4. The process according to claim 1 wherein said solid acid catalyst is silica-alumina.

5. The process according to claim 1 wherein the reaction temperature is from 50° C. to less than 150° C.

6. A process for preparing 2,6-diethylnaphthalene, which comprises reacting at least one kind of feed naphthalene selected from naphthalene and 2-ethylnaphthalene with one or more kinds of polyethylbenzenes selected from diethylbenzenes, triethylbenzenes, tetraethylbenzenes, pentaethylbenzenes, and hexaethylbenzene at 50° to 200° C. in the presence of a solid acid catalyst having pores with a diameter of 7.2 Å or more and containing 0.1 mol/kg or more of acid sites with a differential heat of adsorption of ammonia of 85 kjoul/mol or more, and wherein a ratio of 2,6-diethylnaphthalene to 2,7-diethylnaphthalene in the product is 1.5 or more.

7. The process according to claim 6 wherein said solid acid catalyst is a zeolite having the structure of a faujasite.

8. The process according to claim 6 wherein the reaction temperature is from 50° C. to less than 150° C.

9. The process according to claim 1, wherein said solid acid catalyst is a zeolite having the structure of a faujasite.

10. The process according to claim 6 wherein said solid acid catalyst is a zeolite which has the structure of zeolite Y.

11. The process according to claim 6 wherein said solid acid catalyst is silica-alumina.

* * * * *